United States Patent
Zrenner et al.

(10) Patent No.: US 6,761,724 B1
(45) Date of Patent: *Jul. 13, 2004

(54) METHOD AND DEVICE FOR ENTERING THE SUBRETINAL REGION OF THE EYE

(75) Inventors: Eberhart Zrenner, Tübingen (DE); Veit-Peter Gabel, Regensburg (DE); Karin Kobuch, Pentling (DE)

(73) Assignee: Eberhard-Karls-Universität Tübingen Universitätsklinikum, Tübingen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/528,684

(22) Filed: Mar. 20, 2000

Related U.S. Application Data

(63) Continuation-in-part of application No. PCT/EP98/05953, filed on Sep. 18, 1998.

(30) Foreign Application Priority Data

Sep. 19, 1997 (DE) .......................... 197 41 487

(51) Int. Cl.[7] .................................................. A61F 9/00
(52) U.S. Cl. ..................................................... 606/166
(58) Field of Search .......................... 606/1, 166, 167, 606/170, 15, 16, 17, 4, 107, 48–50, 41; 604/22

(56) References Cited

U.S. PATENT DOCUMENTS

| 4,136,459 A | * | 1/1979 | Suss ........................... 33/567 |
|---|---|---|---|
| 4,452,235 A | * | 6/1984 | Reynolds .................... 606/166 |
| 4,641,648 A | | 2/1987 | Shapiro |
| 4,722,724 A | | 2/1988 | Schocket |
| 4,747,393 A | | 5/1988 | Medwid |
| 5,090,955 A | * | 2/1992 | Simon ........................ 606/166 |
| 5,370,652 A | | 12/1994 | Kellan |
| 5,507,807 A | | 4/1996 | Shippert |
| 5,562,691 A | * | 10/1996 | Tano et al. ................ 606/166 |
| 5,578,040 A | * | 11/1996 | Smith .......................... 606/41 |
| 5,611,799 A | * | 3/1997 | Smith .......................... 606/32 |
| 5,643,437 A | * | 7/1997 | Dong et al. ................ 205/348 |
| 5,651,783 A | * | 7/1997 | Reynard ...................... 606/4 |
| 5,688,264 A | * | 11/1997 | Ren et al. .................... 606/15 |
| 5,817,075 A | * | 10/1998 | Giungo ...................... 660/166 |
| 5,941,250 A | * | 8/1999 | Aramant et al. ............ 128/898 |
| 6,050,999 A | * | 4/2000 | Paraschac et al. ......... 219/636 |
| 6,159,218 A | * | 12/2000 | Aramant et al. ........... 606/107 |

FOREIGN PATENT DOCUMENTS

| DE | 3817112 A | * | 12/1988 | ............. B32B/5/22 |
|---|---|---|---|---|
| EP | 177470 A | * | 4/1986 | ........... B29C/53/50 |
| EP | 0 640 320 A2 | | 12/1991 | |
| EP | 872335 A2 | * | 10/1998 | ........... B32B/15/08 |

\* cited by examiner

Primary Examiner—Michael Peffley
Assistant Examiner—Peter Vrettakos
(74) Attorney, Agent, or Firm—Knobbe, Martens, Olson & Bear, L.L.P.

(57) ABSTRACT

An operation kit is provided for access into the subretinal region of the eye. The kit comprises an elongated flat body of soft material, which can be inserted into the subretinal region from the side through an incision in the sclera. The body is formed as a strip, whose one surface is configured as a guiding surface for a medical device, for example for implanting a microphotodiode chip.

9 Claims, 3 Drawing Sheets

METHOD AND DEVICE FOR ENTERING THE SUBRETINAL REGION OF THE EYE

RELATED APPLICATIONS

This application is a continuation-in-part of International Application PCT/EP98/05953, filed on Sep. 18, 1998.

BACKGROUND OF THE INVENTION

The invention relates to a device for access to the subretinal region of the eye having an elongated flat body of a soft material, which is insertable to the subretinal region through an incision in the sclera of the eye.

A device of this type is disclosed in EP 0 460 320 A2, which is used for placement of a retina implant. It consists of an assembly including a flatly pressed plastic tube as well as a slider located in the plastic tube. To insert the implant, which is in the form of circular, flat microchip, the chip is placed in near the forward opening of the tube. The slider is placed in the tube behind the implant. This assembly is then inserted through an incision in the eye such that the free end of the tube is located at the desired implant location. The tube is then withdrawn with the slider being held fixed, whereby the implant is placed at the desired location.

Two different operation methods are suggested for implantation. In one method, an incision is made in the region of the pars plana and is passed through the vitreous humor of the eye. It is then passed into the subretinal region through an incision made on the vitreous humor side of the retina.

In the other method, an incision is made through the sclera directly behind the ora serrata. The incision is made through the chorioidea, the choriocapillaris, the Bruch membrane as well as the pigment epithelium of the retina, so that the implant can be placed between the inner and outer layers of the retina.

The known device however has the drawback that it is relatively thick and that a control of the positioning is hardly possible. The considerable thickness of the arrangement consisting of a flat tube and the slider is particularly disturbing in the case of entry into the subretinal region because both the retina and the chorioidea are very sensitive and in addition, the chorioidea tends to bleed strongly. The lack of position control is also very detrimental, because retina implants must be positioned precisely and because in other applications requiring access to the subretinal region, it is also important to know the exact position.

SUMMARY OF THE INVENTION

It is a first object of the present invention to provide an improved device which avoids the afore-mentioned disadvantages. It is a second object of the invention to provide a less harmful treatment in the region of the access path. It is a further object of the invention to allow for a precise control of the access positioning.

These and other objects are achieved with a body formed as a strip, whose one surface is configured as a guiding surface for a medical device. The object of the invention is completely achieved in this manner. The use of a strip has the advantage that a very flat construction is possible, while on the other hand, the guiding function is completely maintained. It has now been shown that the guidance over several guiding surfaces in the prior art is not only unnecessary in many applications, it also presents the danger of catching or clamping. This is overcome along with the already mentioned drawback relating to the large size, in particular the thickness of the known device.

In a preferred embodiment of the present invention, the strip is formed as a foil with a thickness of about 30 to 70 μm, preferably about 50 μm. This has the advantage of an extremely thin construction, where however the desired guidance function is completely guaranteed.

In a further preferred embodiment, the strip has a width of about 1 to 5 mm, preferably about 2 mm as well as a length of about 15 to 40 mm, preferably about 25 mm. In further preferred embodiments, the strip is made of plastic, preferably polyethylene or polypropylene, In a further preferred embodiment of the present invention, at least the strip is provided with a scale. This provides the advantage of a precise control of positioning. The control can be provided in that the scale is read relative to the incision in the sclera. However, one can also read the scale relative to the position of the inserted medical device, in particular when it is also provided with a scale or corresponding markings.

Although the present invention is discussed in the following in conjunction with implantation in the subretinal region, it will be understood that the invention can also be applied in several other areas.

The invention is preferably employed with an operation kit for subretinal intervention in the eye, more particularly in that a retina implant is inserted into the subretinal region over the guiding surface of the strip by means of a slider.

In this operation kit, a microsurgical instrument can however also be inserted into the subretinal region over the guiding surface of the strip, where the microsurgical instrument is preferably a laser. In another application of the present invention, a micro-endoscope can be guided to the subretinal region by employing the device of the present invention. The same holds for the insertion of a carrier provided with a drug into the subretinal region of the eye.

Further advantages will become apparent from the following description in conjunction with the attached drawings. It will be understood that the above-mentioned and further features to be discussed below are not only applicable in the given combination, but also apply to other combinations or taken alone without departing from the scope of the present invention.

SHORT DESCRIPTION OF THE DRAWINGS

An embodiment of the present invention will be discussed in the following in more detail in conjunction with the drawings.

DETAILED DESCRIPTION OF THE PREFERRED EMBODIMENTS

Figure 1:
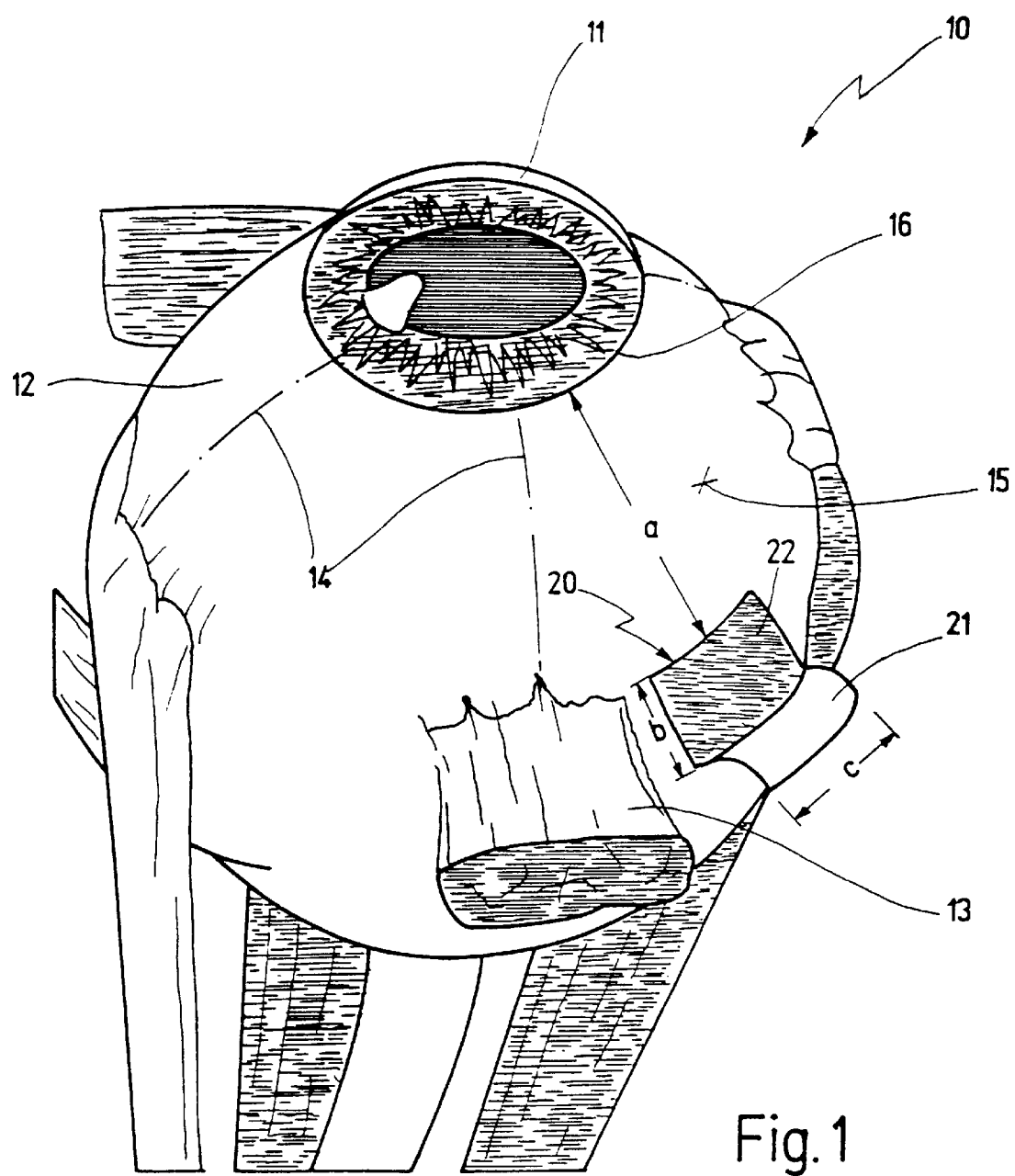
FIG. 1 shows a perspective side view of an eye prepared for operation.
Figure 4:
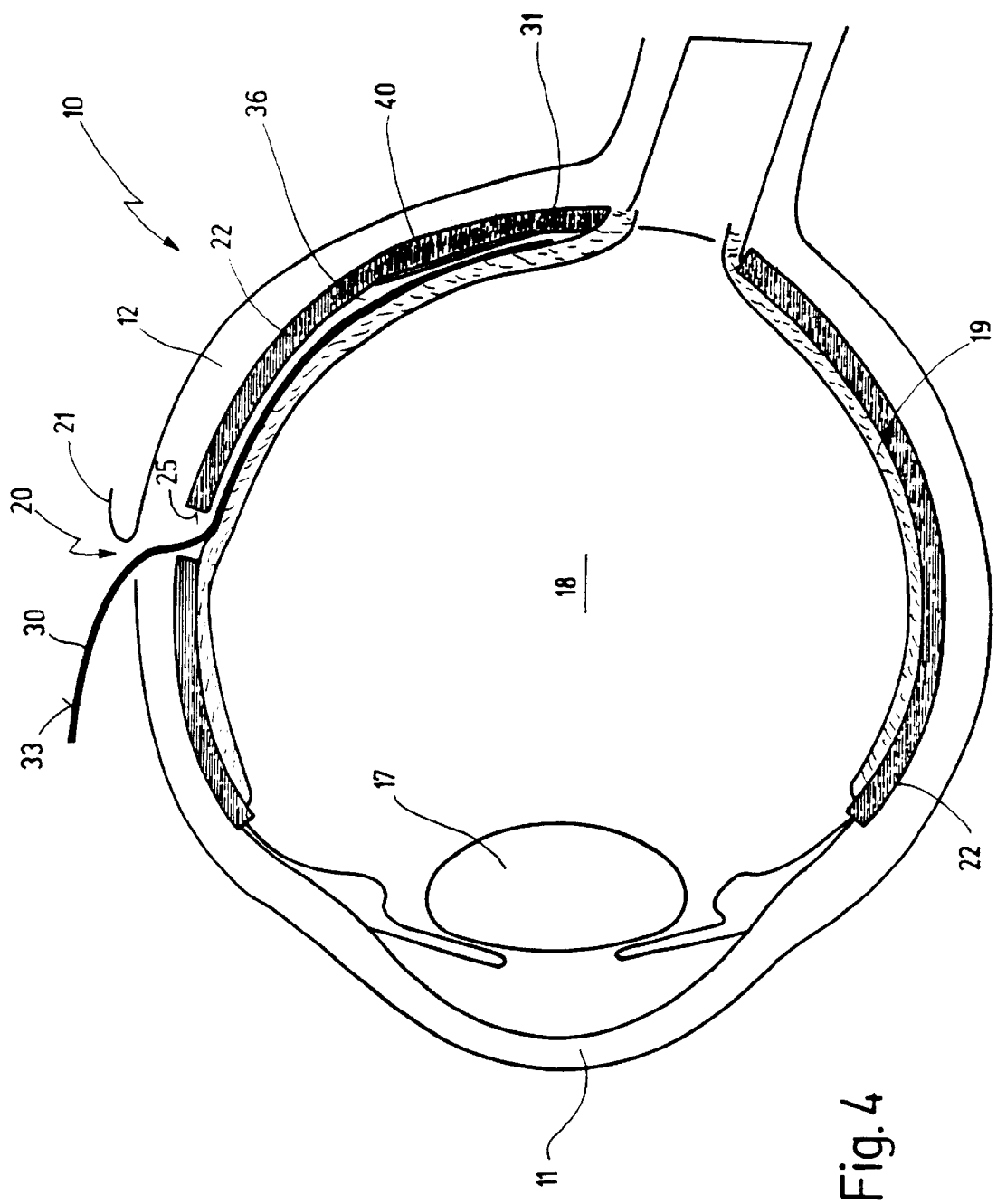
FIG. 4 shows a schematic cross-section through an eye.

The numeral 10 designates an eyeball in the figures. The eyeball 10 comprises a cornea 11 on its front side and a sclera 12 at the remaining surface. The musculus rectus superior is shown in FIG. 1 at the front of the eyeball 10. Four quadrants are drawn with dot dashed lines 14 on the surface of the eyeball 10. The outer, upper quadrant 15 is of interest here. The limbus corneae, i.e. the edge region of the cornea 11 is indicated in FIG. 1 with the numeral 16. FIG. 4 shows the lens as well as the vitreous humor of the eye, behind which the retina 19 is located.

In conventional operations in the subretinal region, access is made through the vitreous humor 18 and through the retina 19. According to the present invention, however, a sclera incision 20 is made in the outer, upper quadrant 15 as clearly shown is FIG. 1. The sclera incision 20 is rectangular, namely at a distance a of preferably 7 to 8 mm from the limbus. The sclera incision 20 produces the sclera flap 21 with a width b and a length c, which is preferably 4 by 4 mm in size. The chorioidea becomes visible beneath the flap 21.

Figure 3:
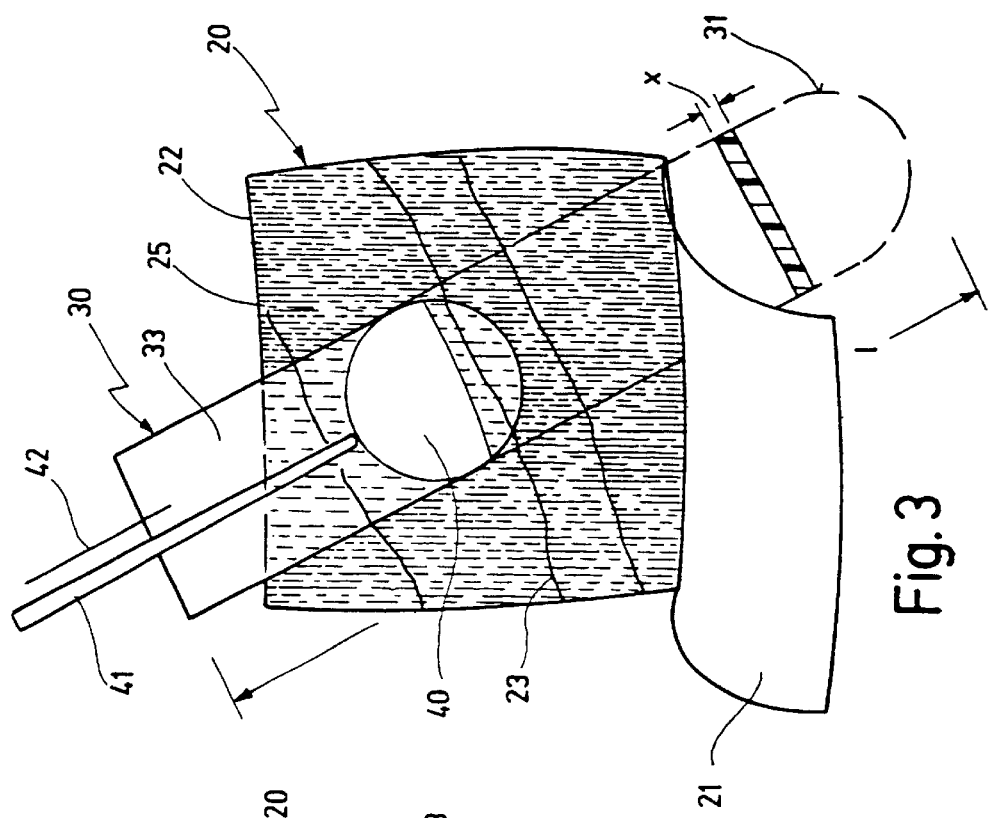
FIGS. 2 and 3 show an enlarged illustration of a region of the eye from FIG. 1 for demonstrating two steps of a method in which the invention is preferably employed.
Figure 2:
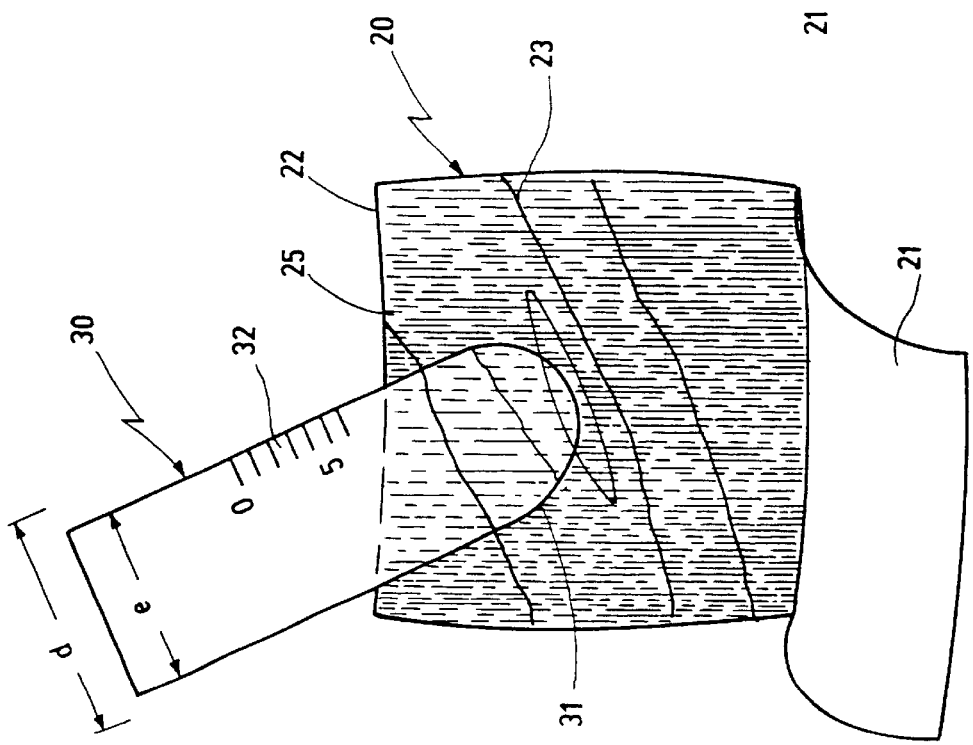

As seen in the enlarged FIGS. 2 and 3, an incision 25 is now made through the chorioidea 22, preferably parallel to the chorioideal vessels 23. The incision 25 has a width d of preferably 2.5 to 3.5 mm. The foil strip 30 can now be passed through the incision 25, which has a somewhat smaller width e of for example 2 mm. In addition, the foil strip 30 has a length 1 of preferably 25 mm and a thickness x of only 50 μm. It is rounded at its front end 31.

The foil strip 30 can be provided with a scale 32 to allow a direct reading of depth at which the strip 30 is inserted into the incision 25. The surface 33 of the strip 30 serves as a guiding surface which will be explained more fully below. As can be seen from the cross-section in FIG. 4, the foil strip 30 has been inserted through the sclera incision 20 and the incision 25 of the chorioidea 22 and into the subretinal region 36. An implant, for example a multiphotodiode array 40 can now be inserted into the subretinal region 36 with a slider 41 (FIG. 3). A plastic tube is preferably employed as the slider 41. The slider 41 can also be provided with a scale. The direction of sliding is indicated with 42 in FIG. 3.

With the above-described means, a so-called "ab externo" implantation of an implant can be carried out as follows:

After cutting through the conjectiva and preparation of the bulbus wall in the outer upper quadrant 15, the musculus rectus superior 13 and the lateralis are employed as anchoring means. At a distance of 8 mm from the limbus 16, a sclera flap 21 is prepared temporally with an edge length of 4 mm. Depending on the experience of the operator and the accessibility of the operation area, the sclera incision 20 can be reduced to a length of 6 mm in the assumed direction of the chorioideal vessels 23.

The intraocular pressure is reduced by a paracentese, so that the chorioidea 22 is no longer bulged in the region of the sclera flap 21. To achieve a local vascular constriction, a drop of Ornipressin (dilution 0.5 I.E./ml) is applied to the chorioidea 22. The chorioidea 22 is then cut at a length d of 2 mm along the direction of the large vessels 23. The foil strip 30, preferably of 2 mm width and rounded at its front end, is placed on the neurosensor-containing retina 19, drawn back to the edge of the chorioidectomy, and then pushed into the subretinal region 36.

The implant, namely a microphotodiode chip 40, is placed on the strip 30 and inserted into the subretinal region 36 along the strip 30. The subretinal position of the chip 40 can be derived from the implantation direction along the foil strip 30 and the length of the inserted foil, without direct intraocular observance. The foil is then withdrawn from the subretinal region 36 to protect the retina 19 and the chorioidea 22 and to avoid retina incarceration in the incision area, however is left on the retina 19 and chorioidea 22 while the stitches in the sclera are made.

In the described operation, a direct, transscleral, transchoroidal access to the subretinal region is possible without opening the intraocular region. In this manner, operation risks of vitrectomy and retinotomy are substantially avoided, in particular a cataract, an ablatio and PVR.

The access obtained by the present invention into the subretinal region can also be employed in other clinical situations, for example in subretinal neovascularisation, bleeding and membranes, implantations and explantations of microphotodiode chips, transplantations of pigment epithelium and retina tissue as well as the subretinal application of drugs. A precise placement of the chip or drugs or micro instruments ab externo at a defined position in the subretinal region is made possible in this manner without direct intraocular observance. In another clinical application of the external access described above, a micro-endoscope of for example 0.9 mm diameter, including flushing channel and the option of an integrated laser or micro-gripper, can be introduced into the subretinal region on the foil. With a reduced flushing with saline solution, a fiber optic resolution (6,000 pixel) of the chip in the subretinal region is possible. One can for example determine the precise position of the chip, optionally exchange the chip or undertake other microsurgical procedures under control of the subretinal endoscope, when the micro instruments are integrated into the endoscope such as cutting means, gripping means or a laser.

What is claimed is:

1. A method of introducing a medical device to a position within a subretinal region of an eye, having a sclera, an intraocular region, a chorioidea, and a retina, comprising the following steps:

providing a side incision in the sclera;

providing an incision in the underlying chorioidea;

inserting an elongated flat strip of flexible material having a guiding surface through the side incisions in the sclera and chorioidea into the subretinal region of the eye;

sliding said flat strip between the chorioidea and the retina to the position, without opening the intraocular region of the eye;

introducing the medical device through the side incisions in the sclera and chorioidea and into the subretinal region of the eye; and guiding the medical device along the guiding surface of the flat strip to the position within the subretinal region of the eye.

2. The method of claim 1, wherein the incision of the sclera is made at a distance of about 6 to 9 mm from the limbus corneae.

3. The method of claim 1, wherein the incision through the chorioidea is made with a width of about 2.5 to 3.5 mm.

4. A method of introducing a medical device into an eye, comprising:

providing a side incision in a sclera, wherein the incision of the sclera is approximately rectangular with dimensions of about 4 by 4 mm;

opening a sclera flap;

providing an incision in an underlying chorioidea;

inserting an elongated flat strip of flexible material having a surface through the incision of the chorioidea into a subretinal region of the eye while guiding said flat strip between the chorioidea and the retina; and introducing the medical device, into the subretinal region of the eye while guiding the medical device along the surface facing the chorioidea.

5. A method of operating on an eye, said eye having a sclera, a chorioidea underlying said sclera and a subretinal region with a retina underlying said chorioidea, the method comprising:

providing a first incision into a side of said sclera;

opening a flap in said sclera along said first incision;

providing a second incision in said chorioidea within said first incision;

inserting an elongated flat strip of flexible material through said second incision into said subretinal region and guiding said strip between said chorioidea and said retina, without opening the intraocular region of the eye, said strip having a guiding surface; and introducing said medical device into said subretinal region by guiding said medical device along said guiding surface on a side facing said chorioidea.

6. The method of claim 5, wherein said eye has a limbus corneae and said first incision is made at a distance of about 6 to 9 mm from said limbus corneae.

7. The method of claim 5, wherein said first incision is approximately rectangular with dimensions of about 4 by 4 mm.

8. The method of claim 5, wherein said second incision is made with a width of about 2.5 to 3.5 mm.

9. The method of claim 5, wherein a retina implant is introduced into said subretinal region.

* * * * *